United States Patent
Gers-Barlag et al.

(10) Patent No.: US 6,815,453 B1
(45) Date of Patent: Nov. 9, 2004

(54) COSMETIC AND DERMATOLOGICAL LIGHT PROTECTION FORMULATIONS HAVING A CONTENT OF TRIAZINE DERIVATIVES AND GLYCERYL COMPOUNDS

(75) Inventors: Heinrich Gers-Barlag, Hamburg (DE); Rainer Kröpke, Hamburg (DE); Anja Müller, Hamburg (DE)

(73) Assignee: Beiersdorf AG, Hamburg (DE)

( * ) Notice: Subject to any disclaimer, the term of this patent is extended or adjusted under 35 U.S.C. 154(b) by 22 days.

(21) Appl. No.: 09/265,779

(22) Filed: Mar. 10, 1999

Related U.S. Application Data

(62) Division of application No. 08/788,147, filed on Jan. 24, 1997, now Pat. No. 5,968,483.

(30) Foreign Application Priority Data

Jan. 25, 1996 (DE) ............................. 196 02 618

(51) Int. Cl.⁷ ................... A61K 31/47; A61K 7/42; A61K 7/44
(52) U.S. Cl. .................... 514/310; 424/59; 424/60
(58) Field of Search ................... 514/310; 424/59, 424/60

(56) References Cited

U.S. PATENT DOCUMENTS

| | | |
|---|---|---|
| 4,070,450 A | 1/1978 | Barner et al. |
| 4,724,137 A | 2/1988 | Hoppe |
| 5,489,431 A | 2/1996 | Ascione et al. |
| 5,968,483 A * | 10/1999 | Gers-Barlag et al. ......... 424/59 |

FOREIGN PATENT DOCUMENTS

| | | |
|---|---|---|
| EP | 457687 | 11/1991 |
| EP | 685223 | 12/1995 |
| EP | 689828 | 1/1996 |

OTHER PUBLICATIONS

Derwent Publications, Abstract JP 04 178 316 A.
Seifen, Ole, Fette, Wachse, UV–Filter für Haut– und Productschutz in Kosmetischen Formulierungen, Bd. 115, No. 18 (1989) pp. 661–662.

* cited by examiner

*Primary Examiner*—Samuel Barts
*Assistant Examiner*—Howard V. Owens
(74) *Attorney, Agent, or Firm*—Norris McLaughlin & Marcus PA

(57) ABSTRACT

Active compound combinations, which have a light protection action, of 4,4',4"-(1,3,5-triazine-2,4,6-triyltriimino)-trisbenzoic acid tris(2-ethylhexyl ester) and one or more emulsifiers chosen from the group of substances of the general structural formula

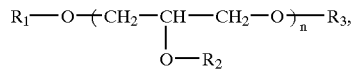

wherein $R_1$, $R_2$ and $R_3$ independently of one another are chosen from the group which comprises: H and branched and unbranched, saturated and unsaturated fatty acid radicals having 8 to 24 carbon atoms, in which up to three aliphatic hydrogen atoms can be replaced by hydroxyl groups, and n is a number from 2 to 8.

10 Claims, No Drawings

COSMETIC AND DERMATOLOGICAL LIGHT PROTECTION FORMULATIONS HAVING A CONTENT OF TRIAZINE DERIVATIVES AND GLYCERYL COMPOUNDS

This is a division of U.S. Ser. No. 08/788,147, filed Jan. 24, 1997, now U.S. Pat. No. 5,968,483, now allowed.

The present invention relates to cosmetic and dermatological light protection formulations, in particular skin-care cosmetic and dermatological light protection formulations.

The damaging effect of the ultraviolet part of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even burns of greater or lesser severity.

The narrower range around 308 nm is stated as the erythema activity maximum of sunlight.

Numerous compounds are known for protection against UVB radiation, these usually being derivatives of 3-benzylidinecamphor, of 4-aminobenzoic acid, of cinnamic acid, of salicylic acid, benzophenone and also of 2-phenylbenzimidazole.

For the range between about 320 nm and about 400 nm, the so-called UVA range, it is also important to have available filter substances, since the rays thereof can also cause damage. Thus, it has been proved that UVA radiation leads to damage to the elastic and collagenic fibres of connective tissue, which makes the skin age prematurely, and that it is to be regarded as a cause of numerous phototoxic and photoallergic reactions. The damaging effect of UVB radiation can be intensified by UVA radiation.

However, UV radiation can also lead to photochemical reactions, the photochemical reaction products then intervening in the skin metabolism.

Such photochemical reaction products are chiefly free-radical compounds, for example hydroxyl radicals. Undefined free-radical photoproducts which are formed in the skin itself can also show uncontrolled secondary reactions because of their high reactivity. However, singlet oxygen, a non-radical excited state of the oxygen molecule, may also occur under UV irradiation, as can short-lived epoxides and many others. Singlet oxygen, for example, is distinguished from the triplet oxygen normally present (free-radical ground state) by an increased reactivity. Nevertheless, excited, reactive (free-radical) triplet states of the oxygen molecule also exist.

UV radiation is furthermore counted among ionizing radiation. There is therefore the risk of ionic species also being formed during UV exposure, which then in turn are capable of intervening oxidatively in biochemical processes.

An advantageous UVB filter is 4,4',4"-(1,3,5-triazine-2, 4,6-triyltriimino)-trisbenzoic acid tris(2-ethylhexyl ester), synonym: 2,4,6-tris-[anilino-(p-carbo-2'-ethyl-1'-hexyloxy)]-1,3,5-triazine.

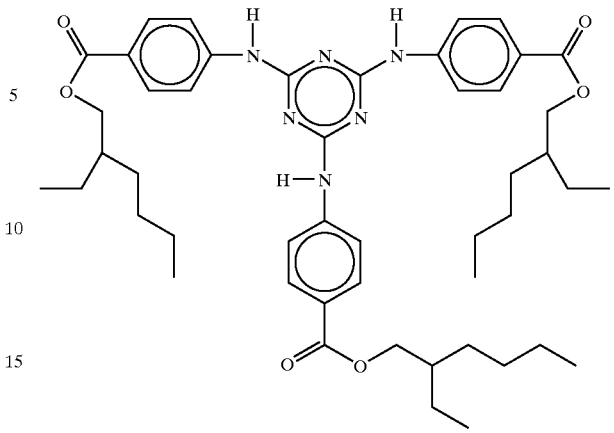

This UVB filter substance is marketed by BASF Aktiengesellschaft under the trade name UVINUL® T 150, and is distinguished by good UV absorption properties.

The main disadvantage of this UVB filter is the poor solubility in lipids. Known solvents for this UVB filter can dissolve a maximum of about 15% by weight of this filter, corresponding to about 1–1.5% by weight of dissolved, and therefore active, UV filter substance.

It was surprising, however, and unforeseeable to the expert that active compound combinations, which have a light protection action, of 4,4',4"-(1,3,5-triazine-2,4,6-triyltriimino)-trisbenzoic acid tris(2-ethylhexyl ester) and one or more emulsifiers chosen from the group of substances of the general structural formula

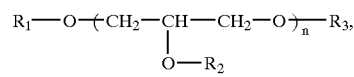

wherein $R_1$, $R_2$ and $R_3$ independently of one another are chosen from the group which comprises: H and branched and unbranched, saturated and unsaturated fatty acid radicals having 8 to 24 carbon atoms, in which up to three aliphatic hydrogen atoms can be replaced by hydroxyl groups, and n is a number from 2 to 8, remedy the disadvantages of the prior art.

The invention also particularly relates to the use of one or more emulsifiers chosen from the group of substances of the general structural formula

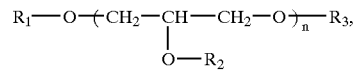

wherein $R_1$, $R_2$ and $R_3$ independently of one another are chosen from the group which comprises: H and branched and unbranched, saturated and unsaturated fatty acid radicals having 8 to 24 carbon atoms, in which up to three aliphatic hydrogen atoms can be replaced by hydroxyl groups, and n is a number from 2 to 8, as a solvent, solubilizing agent or solubilizer for 4,4',4"-(1,3,5-triazine-2,4, 6-triyltriimino)-trisbenzoic acid tris(2-ethylhexyl ester), in particular for use in light protection compositions.

A prerequisite for the usability of the active compound combinations according to the invention for the purposes according to the invention is of course cosmetic or dermatological acceptability of the substances on which they are based.

It is possible, according to the invention, to increase the amounts of 4,4',4"-(1,3,5-triazine-2,4,6-triyltriimino)-trisbenzoic acid tris(2-ethylhexyl ester) employed in cosmetic or dermatological formulations considerably with respect to the prior art.

It was furthermore astonishing that by addition of emulsifiers used according to the invention, chosen from the group of substances of the general structural formula

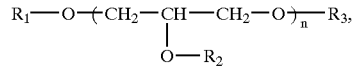

wherein $R_1$, $R_2$ and $R_3$ independently of one another are chosen from the group which comprises: H and branched and unbranched, saturated and unsaturated fatty acid radicals having 8 to 24 carbon atoms, in which up to three aliphatic hydrogen atoms can be replaced by hydroxyl groups, and n is a number from 2 to 8, a stabilization of solutions of 4,4',4"-(1,3,5-triazine-2,4,6-triyltriimino)-trisbenzoic acid tris(2-ethylhexyl ester) is effected, since the latter substance not only has a poor solubility but also readily crystallizes out again from its solution.

The invention therefore also relates to a process for stabilizing solutions of 4,4',4"-(1,3,5-triazine-2,4,6-triyltriimino)-trisbenzoic acid tris (2-ethylhexyl ester), characterized in that an active content of emulsifiers used according to the invention is added to such solutions.

The emulsifier "polyglyceryl 2-polyhydroxy-stearate", which is filed under registration numbers 156531-21-4 and 144470-58-6 in "Chemical Abstracts" and which is obtainable, for example, under the trade name DEHYMULS® PGPH from Henkel KGaA has proved to be especially advantageous.

Japanese laid-open specification JP-H i-04/178316 indeed describes cosmetic formulations having a content of emulsifiers which fall under the structural formula given under (b), but no indication of the present invention is given therein.

The total amount of 4,4',4"-(1,3,5-triazine-2,4,6-triyltriimino)-trisbenzoic acid tris(2-ethylhexyl ester) in the finished cosmetic or dermatological formulations is advantageously chosen from the range of 0.1–10.0% by weight, preferably 0.5–6.0% by weight, based on the total weight of the formulations.

The total amount of one or more emulsifiers used according to the invention, chosen from the group of substances of the general structural formula

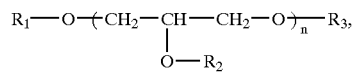

wherein $R_1$, $R_2$ and $R_3$ independently of one another are chosen from the group which comprises: H and branched and unbranched, saturated and unsaturated fatty acid radicals having 8 to 24 carbon atoms, in which up to three aliphatic hydrogen atoms can be replaced by hydroxyl groups, and n is a number from 2 to 8, in the finished cosmetic or dermatological formulations is advantageously chosen from the range of 0.01–250.0% by weight, preferably 0.5–6.0% by weight, based on the total weight of the formulations.

It is advantageous to choose weight ratios of 4,4',4"-(1,3,5-triazine-2,4,6-triyltriimino)-trisbenzoic acid tris(2-ethylhexyl ester) and one or more emulsifiers used according to the invention, chosen from the group of substances of the general structural formula

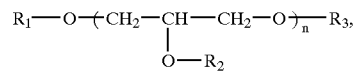

wher in $R_1$, $R_2$ and $R_3$ independently of one another are chosen from the group which comprises: H and branched and unbranched, saturated and unsaturated fatty acid radicals having 8 to 24 carbon atoms, in which up to three aliphatic hydrogen atoms can be replaced by hydroxyl groups, and n is a number from 2 to 8, from the range from 1:10 to 10:1, preferably 1:4 to 4:1.

Cosmetic and dermatological formulations according to the invention moreover comprise inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) or cerium (for example $Ce_2O_3$), mixed oxides of the corresponding metals and mixtures of such oxides. The pigments are particularly preferably those based on $TiO_2$.

It is particularly advantageous in the context of the present invention if the inorganic pigments are present in hydrophobic form, i.e. they are given a water-repellent treatment on the surface. This surface treatment can comprise providing the pigments with a thin hydrophobic layer by processes known per se.

Such a process comprises, for example, producing the hydrophobic surface layer by a reaction in accordance with n $TiO_2$+m $(RO)_3Si-R' \rightarrow$ n $TiO_2$ (surface). n and m in this equation are stoichiometric parameters to be inserted as required, and R and R' are the desired organic radicals. Pigments hydrophobicized, for example, analogously to German Offenlegungsschrift 33 14 742 are of advantage.

Advantageous $TiO_2$ pigments are obtainable, for example, under the trade name MT 100 T from TAYCA.

The total amount or inorganic pigments, in particular hydrophobic inorganic micropigments, in the finished cosmetic or dermatological formulations is advantageously chosen from the range of 0.1–30% by weight, preferably 0.1–10.0, preferably 0.5–6.0% by weight, based on the total weight of the formulations.

The cosmetic and/or dermatological light protection formulations according to the invention can have the customary compositions and be used for cosmetic and/or dermatological protection from light, and furthermore for treatment, care and cleansing of the skin and/or hair and as a make-up product in decorative cosmetics.

For use, the cosmetic and dermatological formulations according to the invention are applied to the skin and/or hair in an adequate amount in the manner customary for cosmetics.

Those cosmetic and dermatological formulations which are in the form of a sunscreen composition are particularly preferred. These can advantageously additionally comprise at least one further UVA filter and/or at least one further UVB filter and/or at least one inorganic pigment, preferably an inorganic micropigment.

The cosmetic and dermatological formulations according to the invention can comprise cosmetic auxiliaries such as are usually used in such formulations, for example preservatives, bactericides, perfumes, substances for preventing foaming, dyestuffs, pigments which have a colouring action, thickeners, moisturizing and/or humectant substances, fats, oils, waxes or other customary constituents of a cosmetic or dermatological formulation, such as alcohols, polyols, polymers, foam stabilizers, electrolytes, organic solvents or silicone derivatives.

An additional content of antioxidants is in general preferred. All the antioxidants suitable or customary for cosmetic and/or dermatological uses can be used according to the invention as favourable antioxidants.

The antioxidants are advantageously chosen from the group consisting of amino acids (for example glycine, histidine, tyrosine and tryptophan) and derivatives thereof, imidazoles (for example urocaninic acid) and derivatives thereof, peptides, such as D,L-carnosine, D-carnosine, L-carnosine and derivatives thereof (for example anserine), carotinoids, carotenes (for example α-carotene, β-carotene and lycopene) and derivatives thereof, chlorogenic acid and derivatives thereof, liponic acid and derivatives thereof (for example di-hydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl cholesteryl and glyceryl esters thereof) and salts thereof, dilauryl thiodipropionate, distearyl thiodipropionate, thiodiproprionic acid and derivatives thereof (esters, ethers, peptides, lipids, nucleotides, nucleosides and salts) and sulphoximine compounds (for example buthionine-sulphoximines, homocysteinesulphoximine, buthionine-sulphones and penta-, hexa- and heptathionine-sulphoximine) in very low tolerated dosages (for example pmol to µmol/kg), and furthermore (metal) chelators (for example α-hydroxy-fatty acids, palmitic acid, phytic acid and lactoferrin), α-hydroxy acids (for example citric acid, lactic acid and maleic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, furfurylidenesorbitol and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosyl-rutin, ferulic acid, furfurylideneglucitol, carnosine, butylhydroxytoluene, butylhydroxyanisole, nordihydroguaiac resin acid, nordihydroguaiaretic acid, trihydroxy-butyrophenone, uric acid and derivatives thereof, mannose and derivatives thereof, zinc and derivatives thereof (for example ZnO and $ZnSO_4$), selenium and derivatives thereof (for example seleniummethionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

The amount of the abovementioned antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

The lipid phase can advantageously be chosen from the following group of substances:
mineral oils, mineral waxes
oils, such as triglycerides of capric or caprylic acid, but preferably castor oil;
fats, waxes and other naturally occurring and synthetic fat substances, preferably esters of fatty acids with alcohols of low C number, for example with isopropanol, propylene glycol or glycerol, or esters of fatty alcohols with alkanoic acids of low C number of with fatty acids;
alkyl benzoate;
silicone oils, such as dimethylpolysiloxanes, di-ethylpolysiloxanes, diphenylpolysiloxanes and mixed forms thereof.

If appropriate, the aqueous phase of the formulations according to the invention advantageously comprises
alcohols, diols or polyols of low C number, and ethers thereof, preferably ethanol, isopropanol, propylene glycol, glycerol, ethyl ne glycol, ethyl ne glycol monoethyl or monobutyl ether, propylene glycol monomethyl, monoethyl or monobutyl ether, diethylene glycol monom thyl or monoethyl ether and analogous products, and furthermore alcohols of low C number, for example ethanol, isopropanol, 1,2-propanediol, glycerol and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of the so-called carbopols, for example carbopols of types 980, 981, 1382, 2984 and 5984, in each case individually or in combination.

The cosmetic or dermatological light protection formulations advantageously comprise inorganic pigments, in particular micropigments, for example in amounts of 0.1% by weight to 30% by weight, preferably in amounts of 0.5% by weight to 10% by weight, but in particular 1% by weight to 6% by weight, based on the total weight of the formulations.

It is advantageous according to the invention to employ, in addition to the combinations according to the invention, oil-soluble UVA filters and/or UVB filters in the lipid phase and/or water-soluble UVA filters and/or UVB filters in the aqueous phase.

The light protection formulations according to the invention can advantageously comprise further substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic formulations which protect the skin from the entire range of ultraviolet radiation. They can also be used as sunscreen compositions.

The further UVB filters can be oil-soluble or water-soluble. Advantageous oil-soluble UVB filter substances are, for example:
3-benzylidenecamphor derivatives, preferably 3-(4-methylbenzylidene) camphor, 3-benzylidenecamphor;
4-aminobenzoic acid derivatives, preferably 2-ethylhexyl 4-(dimethylamino)benzoate and amyl 4-(dimethylamino benzoate;

ester of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone; and esters of benzalmalonic acid, preferably di(2-ethylhexyl) 4-methoxybenzalmalonate.

Advantageous water-soluble UVB filter substances are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and salts thereof; and sulphonic acid derivatives of 3-benzylidenecamphors, such as, for example, 4-(2-oxo-3-bornylidenemethyl) benzenesulphonic acid, 2-methyl-5-(2-oxo-3-bornylidenemethyl) benzenesulphonic acid and salts thereof.

The list of further UVB filters mentioned which can be used in combination with the active compound combinations according to the invention is, of course, not intended to be limiting.

It may also be advantageous to combine the combinations according to the invention with further UVA filters which have usually been contained to date in cosmetic formulations. These substances are preferably derivatives of dibenzoylmethane, in particular 1-(4'-tert-butylphenyl)-3-(4'-methoxyphenyl)-propane-1,3-dione and 1-phenyl-3-(4'-isopropylphenyl)propane-1, 3-dione. The invention also relates to these combinations and to formulations which comprise these combinations. The amounts used for the UVB combination can be employed.

It is furthermore advantageous to combine the active compound combinations according to the invention with further UVA and/or UVB filters.

It is also particularly advantageous to combine the active compound combinations according to the invention with salicylic acid derivatives, some representatives of which are known, which can likewise absorb UV radiation. The customary UV filters include

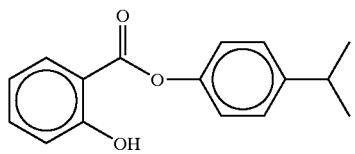

(4-isopropylbenzyl salicylate),

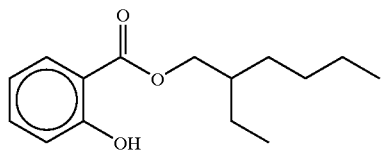

(2-ethylhexyl salicylate, octyl salicylate)

-continued

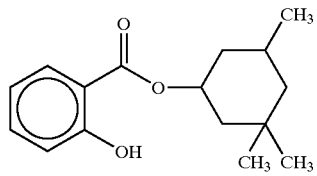

(homomenthyl salicylate).

The invention also relates to a process for the preparation of the cosmetic and/or dermatological light protection formulations according to the invention, which is characterized in that, in a manner known per se, the 4,4',4''-(1,3,5-triazine-2,4,6-triyltriimino)-trisbenzoic acid tris(2-ethylhexyl ester) is suspended in one or more alkanecarboxylic acids or an oily phase having a content of alkanecarboxylic acids, while stirring uniformly and if appropriate while heating, and, if desired, the mixture is homogenized, the mixture is combined with further lipid components, if appropriate, and with one or more emulsifiers, if appropriate, thereafter the oily phase is mixed with the aqueous phase, into which a thickener has been incorporated, if appropriate, and which preferably has about the same temperature as the oily phase, and the mixture is homogenized, if desired, and allowed to cool to room temperature. After cooling to room temperature, the mixture can be homogenized again, especially if volatile constituents are also to be incorporated.

The following examples are intended to illustrate the present invention without limiting it. All the amounts data, contents and percentage contents are based on the weight and the total amount or on the total weight of the formulations, unless stated otherwise.

EXAMPLE 1

| Sun cream | |
|---|---|
| | % by weight |
| Polyglyceryl 2-polyhydroxystearate | 5.00 |
| Softisan 100 | 3.00 |
| Glycerol | 3.00 |
| Lunacera S | 0.50 |
| Magnesium sulphate | 0.70 |
| Mineral oil | 12.00 |
| Caprylyl ether | 8.00 |
| Uvinul T 150 | 3.00 |
| Cetearyl isononanoate | 6.00 |
| Preservative, perfume | q.s. |
| Water, demineralized to | 100.00 |

EXAMPLE 2

| Sunscreen lotion | |
|---|---|
| | % by weight |
| Polyglyceryl 2-polyhydroxystearate | 5.00 |
| Magnesium stearate | 0.05 |
| Butylene glycol | 5.00 |
| Elfacos C26 | 1.00 |
| Magnesium sulphate | 0.50 |
| Isohexadecane | 7.00 |
| Capric/caprylic tryglyceride | 5.00 |
| Cetearylisononanoate | 14.00 |

-continued

Sunscreen lotion

| | % by weight |
|---|---|
| Uvinul T150 | 5.00 |
| Preservative, perfume | q.s. |
| Water, demineralized to | 100.00 |

EXAMPLE 3

| | % by weight |
|---|---|
| Glyceryl lanolate | 1.00 |
| Wool wax alcohol | 0.10 |
| Polyglycerol 2-polyhydroxystearate | 5.00 |
| Paraffin oil (paraffinum liquidum) | 6.00 |
| Isohexadecane | 4.00 |
| Myristyl myristate | 3.00 |
| Butylmethoxydibenzoylmethane | 2.00 |
| Methylbenzylidenecamphor | 4.00 |
| Octyltriazone | 1.50 |
| Titanium dioxide | 2.00 |
| Lactic acid | 1.00 |
| Sodium hydroxide | q.s. |
| Glycerol | 5.00 |
| Alcohol, denatured | 2.00 |
| $MgSO_4$ | 0.70 |
| Bisabolol | 0.10 |
| $Na_3HEDTA$ | 0.50 |
| Tocopheryl acetate | 0.50 |
| Preservative, perfume | q.s. |
| Water to | 100.00 |

What is claimed is:

1. A cosmetic or dermatological composition for protecting skin from the damaging effects of UV light, said composition comprising:

a) a light protective amount of 4,4',4"-(1,3,5-triazine-2,4,6-triyltriimino)-trisbenzoic acid tris (2-ethylhexyl ester); and
   b) an amount of polyglyceryl 2-polyhydroxystearate sufficient to solubilize said light protective amount of 4,4',4"-(1,3,5-triazine-2,4,6-triyltriimino)-trisbenzoic acid tris (2-ethylhexyl ester).

2. A method of protecting skin from the damaging effects of UV light comprising applying to the skin a light protective amount of a composition according to claim 1.

3. A cosmetic or dermatologic composition according to claim 1, which further comprises at least one additional UVA and/or UVB filter.

4. A cosmetic or dermatologic composition according to claim 1, which further comprises at least one cosmetically or dermatologically acceptable inorganic pigment.

5. A cosmetic or dermatologic composition according to claim 1, which further comprises at least one cosmetically or dermatologically acceptable auxiliary.

6. A cosmetic or dermatologic composition according to claim 1, which further comprises at least one cosmetically or dermatologically acceptable antioxidant.

7. A method according to claim 2, wherein the cosmetic or dermatologic composition further comprises at least one additional UVA and/or UVB filter.

8. A method according to claim 2, wherein the cosmetic or dermatologic composition further comprises at least one cosmetically or dermatologically acceptable inorganic pigment.

9. A method according to claim 2, wherein the cosmetic or dermatologic composition further comprises at least one cosmetically or dermatologically acceptable auxiliary.

10. A method according to claim 2, wherein the cosmetic or dermatologic composition further comprises at least one cosmetically or dermatologically acceptable antioxidant.

* * * * *

UNITED STATES PATENT AND TRADEMARK OFFICE
CERTIFICATE OF CORRECTION

PATENT NO. : 6,815,453 B1
APPLICATION NO. : 09/265779
DATED : November 9, 2004
INVENTOR(S) : H. Gers-Barlag et al.

It is certified that error appears in the above-identified patent and that said Letters Patent is hereby corrected as shown below:

Column 3, Line 37, "JP- Hi-04/178316" should read -- JP-Hei-04/178316 --

Column 4, Line 9, "wher in" should read -- wherein--

Column 6, Line 23, " ethyl ne glycol, ethyl ne glycol" should read -- ethylene glycol, ethylene glycol--

Column 6, Line 26, "monom thyl" should read -- monomethyl--

Column 6, Line 67, "(dimethylamino benzoate;" should read -- (dimethylamino) benzoate; --

Signed and Sealed this

Seventeenth Day of July, 2007

JON W. DUDAS
*Director of the United States Patent and Trademark Office*